US012692550B2

(12) United States Patent
Dietrich et al.

(10) Patent No.: US 12,692,550 B2
(45) Date of Patent: *Jul. 28, 2026

(54) SINGLE-MOLECULE SEQUENCE AND HIGH SENSITIVITY METHYLATION ANALYSIS FOR TISSUE-SPECIFIC ANALYSIS

(71) Applicant: Siemens Healthineers AG, Erlangen (DE)

(72) Inventors: Carsten Dietrich, Nuremberg (DE); Andreas Emanuel Posch, Vienna (AT)

(73) Assignee: Siemens Healthineers AG, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/424,474

(22) Filed: Jan. 26, 2024

(65) Prior Publication Data

US 2024/0200143 A1      Jun. 20, 2024

Related U.S. Application Data

(63) Continuation of application No. 16/487,477, filed as application No. PCT/EP2018/051502 on Jan. 23, 2018, now Pat. No. 11,920,201.

(30) Foreign Application Priority Data

Feb. 23, 2017    (EP) ..................................... 17157619

(51) Int. Cl.
*C12Q 1/6886*      (2018.01)
*C12Q 1/6869*      (2018.01)
(52) U.S. Cl.
CPC ......... *C12Q 1/6886* (2013.01); *C12Q 1/6869* (2013.01); *C12Q 2600/154* (2013.01); *C12Q 2600/156* (2013.01)

(58) Field of Classification Search
CPC ................ C12Q 1/6886; C12Q 1/6869; C12Q 2600/154; C12Q 2600/156
See application file for complete search history.

(56) References Cited

U.S. PATENT DOCUMENTS

| | | | |
|---|---|---|---|
| 5,795,782 | A | 8/1998 | Church et al. |
| 2007/0178474 | A1 | 8/2007 | Cracauer et al. |
| 2013/0189684 | A1 | 7/2013 | Ehrich et al. |
| 2013/0190386 | A1 | 7/2013 | Croce et al. |

(Continued)

FOREIGN PATENT DOCUMENTS

| | | |
|---|---|---|
| WO | 03074730 A1 | 9/2003 |
| WO | 2011070441 A2 | 6/2011 |

(Continued)

OTHER PUBLICATIONS

B.A. Flusberg et al., "Direct detection of DNA methylation during single-molecule, real-time sequencing", Nature Methods 7, 461-465, 2010, doi:10.1038/nmeth.1459.

(Continued)

*Primary Examiner* — Joseph G. Dauner
(74) *Attorney, Agent, or Firm* — Baker Hostetler

(57) ABSTRACT

Provided herein are methods of determining one or more modification(s) of the nucleic acid sequence of at least one nucleic acid and at least one epigenetic alteration of the at least one nucleic acid in a sample of a subject. The sample is derived from a body fluid of the subject. The methods link the one or more modification(s) to a specific cell type.

19 Claims, 3 Drawing Sheets

(56) References Cited

U.S. PATENT DOCUMENTS

2013/0303385 A1   11/2013   Korlach et al.
2016/0017419 A1   1/2016   Chiu et al.

FOREIGN PATENT DOCUMENTS

WO        2013148400 A1     10/2013
WO        2016094813 A1     6/2016
WO        2016127944 A1     8/2016

OTHER PUBLICATIONS

R. Lehmann-Werman et al., "Identification of tissue-specific cell death using methylation patterns of circulating DNA", PNAS, 113, 13. E1826-E1834, doi:10.1073/pnas.1519286113; 2016.

R.P. Darst et al., "Bisulfite Sequencing of DNA"; in: Curr. Protoc. Mol. Biol.; 2010; doi:10.1002/0471142727.mb0709s91; 2010.

John J. Kasianowicz et al., "Characterization of individual polynucleotide molecules using a membrane channel", PNAS 93, 24, 13779-13773, 1996.

Simpson et al., "Detecting DNA Methylation using the Oxford Nanopore Technologies MinION sequencer", https://doi.org/10.1101/047142; Published in bioRxiv Apr. 4, 2016.

Lokk et al., "DNA methylome profiling of human tissues identifies global and tissue-specific methylation patterns", Genome Biology 15:3248; 2014.

K. Sun et al., "Plasma DNA tissue mapping by genome-wide methylation sequencing for noninvasive prenatal, cancer, and transplantation assessments", PNAS, vol. 112 No. 40, E5503-E5512, doi:10.1073/pnas.1508736112; 2014.

B. Zhang et al: "Functional DNA methylation differences between tissues, cell types, and across individuals discovered using the M&M algorithm", Genome Research, vol. 23, No. 9, pp. 1522-1540, XP055457350,US ISSN: 1088-9051, DOI: 10.1101/gr.156539. 113; 2013.

Barturen, Guillermo et al.: MethylExtract: High-Quality methylation maps and SNV calling from whole genome bisulfite sequencing data [version 2; referees: 3 approved]; in: F1000Research; vol. 2; No. 217; 2014; doi: 10.12688/f1000research.2-217.v2.

Sato et al. British Journal of Cancer. 2001. 85(2):199-203 (Year:2001).

Hibi et al. Anticancer Research. 2010. 30:107-110. (Year: 2010).

Lu Hengyun et al: "Oxford Nanopore MinION Sequencing and Genome Assembly"; Genomics Proteomics and Bioinformatics, Beijing Genomics Institute, Beijing, CN, vol. 14, No. 5, pp. 265-279, XP029799460, ISSN: 1672-0229, DOI: 10.1016/J.GPB.2016. 05.004; 2016.

T. Ohshiro et al., "Single-Molecule Electrical Random Resequencing of DNA and RNA", Scientific Reports 2, Article No. 501 (2012), doi:10.1038/srep00501.

Snyder et al., "Cell-free DNA Comprises an In Vivo Nucleosome Footprint that Informs Its Tissues-Of-Origin", Cell 164, 1-2, 57-68, 2016, http://dx.doi.org/10.1016/j.cell.2015.11.050; 2016.

A.M. Newman et al., "Integrated digital error suppression for improved detection of circulating tumor DNA", Nature Biotechnology 34, 547-555, 2016, doi:10.1038/nbt.3520; 2016.

Ensemble (http://www.ensembl.org); 2017.

NIH Roadmap Epigenomics Mapping Consortium; snapshot from Oct. 19, 2016 (http://egg2.wustl.edu/roadmap/web_portal/); 2016. https://www.omim.org/; 2017.

Meissner et al., "Genome-scale DNA methylation maps of pluripotent and differentiated cells", Nature, 454, 766-770, 2008, doi:10.1038/nature07107; 2008.

Montero et al., "Epigenetic inactivation of EGFR by CpG island hypermethylation in cancer" Cancer Bioloav & Therapy 5:11, 1494-1501 (2006).

Yamshita et al. "DCC is a potential methylation marker in human cancers". Journal of Clinical Oncology. 2007. 25(18):suppl 15054-15054. (Year: 2007).

My Cancer Genome: Biomarkers—EGFR L858R. Retrieved on Feb. 8, 2023 from the internet: https://www.mycancergenome.org/content/al teration/egfr -I 858r/#:-:text=Overview& text= E G FR %20 L858 R %20is % 20present%20i n, the%20g reatest% 20prevalence % 20%5B4%5D. (Year: 2023).

Moss et al. Nature Communications. 2018. 9: Article No. 5068. (Year: 2018).

National Cancer Institute, The Cancer Genome Atlas Program, retrieved from https://www.cancer.gov/about-nci/organization/ccg/research/structural-genomics/tcga, accessed Aug. 20, 2019, 2 pages.

SINGLE-MOLECULE SEQUENCE AND HIGH SENSITIVITY METHYLATION ANALYSIS FOR TISSUE-SPECIFIC ANALYSIS

CROSS-REFERENCE TO RELATED APPLICATIONS

This application is a continuation of U.S. application Ser. No. 16/487,477, filed Aug. 21, 2019, which is a 35 U.S.C. § 371 national phase application of International Patent Application No. PCT/EP2018/051502, filed Jan. 23, 2018, which claims priority to European Patent Application No. 17157619.2, filed Feb. 23, 2017, the entire disclosures of which are incorporated herein by reference in their entirety.

FIELD

The present invention relates to methods of determining one or more modification(s) of the nucleic acid sequence of at least one nucleic acid and at least one epigenetic alteration of said at least one nucleic acid in a sample of a subject, wherein the sample is derived from a body fluid of the subject, in order to link the one or more modification to a specific cell type.

BACKGROUND

Liquid biopsy (sequencing of cell free DNA (cfDNA)) is recently thought to replace tissue biopsy by sampling tissues/cells/molecules from a blood sample. This is especially useful when the target tissue is hard to reach/probe and would require large incisions that would leave a patient with large traumas and wounds.

In current non-targeted (open question approach) liquid biopsy, sequencing allows detection of malignant nucleic acid, e.g. DNA, alterations indicative of disease. In this regard, liquid biopsy can be based on cell-free DNA/RNA, exosomes with DNA/RNA, or circulating tumor cells (DNA/RNA. However, the original tissue where analyzed DNA fragments stem from cannot be determined with this approach.

Determination of the tissue of origin would be particularly useful, though, to (i) directly link somatic mutations to the tissue of origin (tumor/metastases) and (ii) determine fibrotic/necrotic tissue by increased cell free DNA levels in the blood. Finally, false positive/negative results might be the result of this workflow, since malignant DNA changes might be nonfunctional (hence not malignant) when occurring in non-relevant tissues, so that also in this regard the determination of the tissue of origin is helpful.

Currently, liquid biopsy needs to be complemented by imaging based diagnostics to identify location of tumors, lesions and/or metastases. For example, Molecular Stethoscope links RNA molecules to tissue. The analysis of somatic DNA changes, however, is almost impossible. Furthermore, the cfRNA (cell free RNA) amount is much less (up to 3 orders of magnitude less) than cfDNA.

Another approach that is taken is the use of epigenetic information from liquid biopsy for determining e.g. tumours, as disclosed e.g. by K. Sun et al., "Plasma DNA tissue mapping by genome-wide methylation sequencing for noninvasive prenatal, cancer, and transplantation assessments", PNAS, vol. 112 no. 40, E5503-E5512, doi:10_1073/pnas 1508736112, wherein the authors use methylation analysis after bisulfite conversion.

Similarly, the company Nucleix, Israel, offers urine based liquid biopsy. A methylation pattern is therein used for identification whether bladder cancer is present or not.

SUMMARY

The present inventors propose a liquid biopsy workflow that also considers epigenetic modifications (e.g. methylation) of the same molecules used for DNA sequencing and thereby achieves two improvements: First, malignant epigenetic changes can be detected in liquid biopsy and the corresponding information used in addition to the information from sequencing, as epigenetic changes can also be causal for diseases and cancer). Second, since epigenetic alterations are among the most important alterations when it comes to cell differentiation, many epigenetic modifications are indicative of a certain cell type. This offers to classify DNA fragments with regard to their original tissue type. Any other detected changes, be it DNA variations or epigenetic variations, can subsequently be analyzed in a tissue-specific manner—hence coming close to a regular biopsy—but without incisions.

In a first aspect the present invention relates to a method of determining one or more modification(s) of the nucleic acid sequence of at least one nucleic acid and at least one epigenetic alteration of said at least one nucleic acid in a sample of a subject, wherein the sample is derived from a body fluid of the subject, comprising:

obtaining or providing a sample from the subject comprising at least one nucleic acid;

sequencing the at least one nucleic acid from the sample to obtain the nucleic acid sequence of said at least one nucleic acid, and determining at least a part of the epigenetic profile of said at least one nucleic acid;

comparing said nucleic acid sequence to a first reference database to determine one or more modification(s) thereof;

comparing the at least part of the epigenetic profile of said at least one nucleic acid to a second reference database to correlate said at least one nucleic acid to a specific cell type; and linking the one or more modification(s) of the at least one nucleic acid sequence to the specific cell type.

A second aspect of the present invention is directed to a method of determining a malignant condition of a specific cell type in a subject, comprising:

obtaining or providing a sample from the subject comprising at least one nucleic acid;

sequencing the at least one nucleic acid from the sample to obtain the nucleic acid sequence of said at least one nucleic acid, and determining at least a part of the epigenetic profile of said at least one nucleic acid;

comparing said nucleic acid sequence to a first reference database to determine one or more modification(s) thereof that are indicative of a malignant condition;

comparing the at least part of the epigenetic profile of said at least one nucleic acid to a second reference database to correlate said at least one nucleic acid to a specific cell type; and linking the one or more modification(s) of the at least one nucleic acid sequence that are indicative of a malignant condition to the specific cell type.

Also disclosed is in a third aspect a method of linking one of more modification(s) of at least one nucleic acid sequence in a sample of a subject to a specific cell type of the subject, comprising:

obtaining or providing at least one nucleic acid sequence of a nucleic acid and at least a part of the epigenetic profile of said at least one nucleic acid;

comparing said nucleic acid sequence to a first reference database to determine one or more modification(s) thereof;

comparing the at least part of the epigenetic profile of said at least one nucleic acid to a second reference database to correlate said at least one nucleic acid to a specific cell type; and linking the one or more modification(s) of the at least one nucleic acid sequence to the specific cell type.

Further, the present invention also relates to a computer program product comprising computer executable instructions which, when executed, perform a method according to the third aspect.

Further aspects and embodiments of the invention are dis-closed in the dependent claims and can be taken from the following description, figures and examples, without being limited thereto.

BRIEF DESCRIPTION OF DRAWINGS

The enclosed drawings should illustrate embodiments of the present invention and convey a further understanding thereof. In connection with the description they serve as explanation of concepts and principles of the invention. Other embodiments and many of the stated advantages can be derived in relation to the drawings. The elements of the drawings are not necessarily to scale towards each other. Identical, functionally equivalent and acting equal features and components are denoted in the figures of the drawings with the same reference numbers, unless noted otherwise.

DETAILED DESCRIPTION OF THE INVENTION

Definitions

Figure 1:
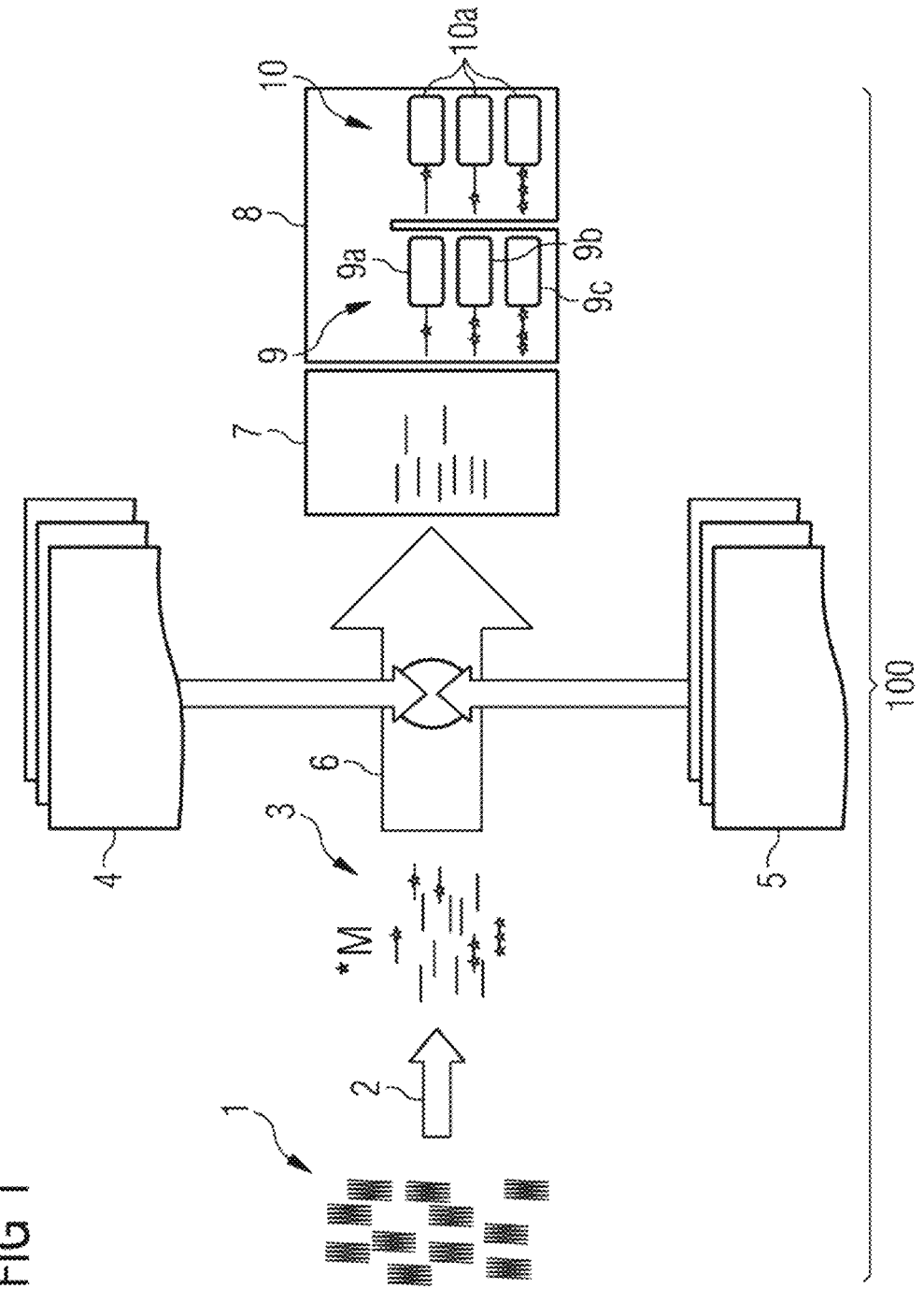
FIG. 1 shows schematically a method of determining simultaneously one or more modification(s) of nucleic acid sequences of circulating DNA and/or RNA molecules and the methylation data thereof to link the modifications to specific cell types in a method of the present invention.

Unless defined otherwise, technical and scientific terms used herein have the same meaning as commonly understood by one of ordinary skill in the art to which this invention belongs.

In the context of the present invention a "sample" is a sample which comprises potentially at least one nucleic acid to be sequenced. Within the scope of the present invention, the sample is derived from a body fluid of a subject, i.e. not from matter that does not represent a body fluid, e.g. organic tissue. Body fluids are thereby liquids originating from inside the bodies of subjects, particularly living subjects. They include fluids that can be excreted or secreted from the body and/or that circulate in the body, and body water. They can be in the state of a liquid, emulsion or suspension. Examples of body fluids within the invention are blood, urine, saliva, sputum, plasma, serum. A sample derived from a body fluid can be the body fluid itself as well as a body fluid that is worked up, e.g. wherein specific parts are extracted, separated, etc. According to certain embodiments, the sample is a patient sample (clinical isolate). Preferred samples are serum, plasma, and/or whole blood of a patient.

According to certain embodiments, the subject in the present methods is a vertebrate, preferably a human or animal, more preferably a mammal and most preferred a human, respectively human patient.

A vertebrate within the present invention refers to animals having a vertebrate, which includes mammals—including humans, birds, reptiles, amphibians and fishes. The present invention thus is not only suitable for humans and the human medical field, but also for veterinary medicine.

The term "nucleic acid" refers to a polynucleotide molecule having a defined sequence. It comprises DNA molecules, RNA molecules, nucleotide analog molecules and combinations and derivatives thereof, such as DNA molecules or RNA molecules with incorporated nucleotide analogs or cDNA. It also comprises cell free (cf) DNA and RNA. The term "nucleic acid sequence" relates to the sequence of nucleotides in the nucleic acid molecule.

The term "modification" of the nucleic acid sequence refers to any change in the nucleic acid sequence, i.e. in the nucleotide sequence, occurring compared to a reference sequence, and does not refer to epigenetic changes, which are herein termed "epigenetic alteration". A modification of the nucleic acid sequence comprises e.g. a mutation, i.e. a variation in the sequence as compared to a reference sequence. Such a reference sequence can be a sequence determined in a predominant wild type organism or a reference organism, e.g. a defined and known reference sequence of an animal or human. A mutation is for example a deletion of one or multiple nucleotides, an insertion of one or multiple nucleotides, or substitution of one or multiple nucleotides, duplication of one or a sequence of multiple nucleotides, translocation of one or a sequence of multiple nucleotides, and a single nucleotide polymorphism (SNP). A modification of the nucleic acid sequence can also refer to e.g. a deletion of a whole gene in a sequence, but can also refer to non-coding sequence in a nucleic acid.

Epigenetics relate to all factors that affect heritable traits that are not related to changes in the nucleic acid sequence, i.e. the nucleotide sequence. It relates to e.g. histones, methylation of nucleic acids (particularly DNA and/or RNA), telomeres, prions, hydroxymethylation, oxidation of nucleotides, etc., which can influence e.g. activity of a gene, respectively gene function, not related to the nucleic acid sequence itself.

An epigenetic profile relates to all factors of a nucleic acid, respectively nucleic acid molecule, not associated with the nucleic acid sequence, particularly affecting downstream physiological processes such as e.g. transcription and thus may result in phenotypic changes. A part of an epigenetic profile relates to only a part of all epigenetic factors associated with a nucleic acid, e.g. the methylation information of the nucleic acid or of a part thereof.

An epigenetic alteration is a change in the epigenetic information of a nucleic acid, i.e. an alteration in a nucleic acid molecule that is not a modification of the nucleic acid sequence, of a cell of a specific cell type compared to one or more cells of other cell types, e.g. also as described in Meissner et al., "Genome-scale DNA methylation maps of pluripotent and differentiated cells", Nature, 454, 766-770, 2008, doi:10_1038/nature07107, and Lokk et al., "DNA methylome profiling of human tissues identifies global and tissue-specific methylation patterns", Genome Biology 15:3248.

Before the invention is described in exemplary detail, it is to be understood that this invention is not limited to the particular component parts of the process steps of the methods described herein as such methods may vary. It is also to be understood that the terminology used herein is for purposes of describing particular embodiments only, and is not intended to be limiting. It must be noted that, as used in the specification and the appended claims, the singular forms "a", "an" and "the" include singular and/or plural referents unless the context clearly dictates otherwise. For example, the term "a" as used herein can be understood as one single entity or in the meaning of "one or more" entities. It is also to be understood that plural forms include singular and/or plural referents unless the context clearly dictates otherwise. It is moreover to be understood that, in case parameter ranges are given which are delimited by numeric values, the ranges are deemed to include these limitation values.

A first aspect of the present invention relates to a method of determining one or more modification(s) of the nucleic acid sequence of at least one nucleic acid and at least one epigenetic alteration of said at least one nucleic acid in a sample of a subject, wherein the sample is derived from a body fluid of the subject, comprising:

obtaining or providing a sample from the subject comprising at least one nucleic acid;

sequencing the at least one nucleic acid from the sample to obtain the nucleic acid sequence of said at least one nucleic acid, and determining at least a part of the epigenetic profile of said at least one nucleic acid;

comparing said nucleic acid sequence to a first reference database to determine one or more modification(s) thereof;

comparing the at least part of the epigenetic profile of said at least one nucleic acid to a second reference database to correlate said at least one nucleic acid to a specific cell type; and linking the one or more modification(s) of the at least one nucleic acid sequence to the specific cell type.

In the present methods, the sample can be provided or obtained from the subject in any way, preferably non-invasive, and can be e.g. provided as an in vitro sample or prepared as in vitro sample.

The sequencing of the at least one nucleic acid from the sample is not particularly limited and can be done by any suitable sequencing method.

Further, also the determination of the at least part of the epigenetic profile of the nucleic acid is not particularly limited and can be done by any suitable method as well.

In this regard, it is only important that the determining of the nucleic acid sequence of the nucleic acid and the determining of the at least part of the epigenetic profile of the nucleic acid are carried out on the at least one nucleic acid. i.e. the same molecule.

According to certain embodiments, the sequencing of the at least one nucleic acid and the determination of the at least part of the epigenetic profile are carried out at the same time by a suitable method that can provide the nucleic acid sequence of a nucleic acid and at the same time obtain at least a part of the epigenetic data of the same nucleic acid. e.g. the information regarding methylation of the nucleic acid. According to certain embodiments, the sequencing of the at least one nucleic acid from the sample to obtain the nucleic acid sequence of said at least one nucleic acid, and determining at least a part of the epigenetic profile of said at least one nucleic acid is carried out using a method selected from single-molecule based sequencing techniques. e.g.

single-molecule real-time (SMRT) sequencing techniques such as PacBio™ (Pacific Biosciences of California. Inc.) on time-level with optical read-out, as e.g. described by B. A. Flusberg et al., "Direct detection of DNA methylation during single-molecule, real-time sequencing", Nature Methods 7, 461-465, 2010, doi:10_1038/nmeth_1459, for example with nanopore sequencing, as e.g. described in U.S. Pat. No. 5,795,782 and e.g. provided by Oxford Nanopore Technologies, UK, with detection methods such as indirect detection via ion current changes, as e.g. described by B. A. Flusberg et al., "Direct detection of DNA methylation during single-molecule, real-time sequencing", Nature Methods 7, 461-465, 2010, doi:10_1038/nmeth_1459. John J. Kasianowicz et al., "Characterization of individual polynucleotide molecules using a membrane channel", PNAS 93, 24, 13779-13773, 1996, and Simpson et al., "Detecting DNA Methylation using the Oxford Nanopore Technologies MinION sequencer", doi_org/10_1101/047142, or tunneling current, as described by e.g. T. Ohshiro et al., "Single-Molecule Electrical Random Resequencing of DNA and RNA", Scientific Reports 2, Article number: 501 (2012), doi:10_1038/srep00501. However, other methods or combinations thereof are possible. Generally all sequencing methods can be used that can measure base modifications via electrochemical, optical and/or other physico-chemical properties. In contrast to other sequencing methods like bisulfite sequencing, the above methods can provide information of the nucleic acid sequence and at least part of the epigenetic profile at the same time, so that a smaller amount of nucleic acid can be used and that also no artifacts are obtained due to a modification of the nucleic acid, as is e.g. the case during bisulfite sequencing. Due to this approach, also cost can be saved. This aspect is of tremendous use in a method where the nucleic acid is coming from a sample derived from a body fluid of the subject, as in liquid biopsy.

It is not excluded in the present invention that the sample is worked up prior to sequencing the at least one nucleic acid and/or determining at least a part of the epigenetic profile of said at least one nucleic acid, e.g. by isolating the at least one nucleic acid from the sample or at least concentrate it therein by a suitable method, e.g. by centrifuging, e.g. if the sample is a blood sample. However, it is also possible that sequencing and determining at least a part of the epigenetic profile of the nucleic acid is carried out using the sample without prior work-up, i.e. as is.

In the present methods, the first reference database is not particularly limited as long as modifications of a nucleic acid sequence can be determined. It can e.g. comprise nucleic acid sequence information of one or more healthy subject(s) of the same species as the subject of which the sample in the present method is obtained or provided, but can also alternatively or in addition contain nucleic acid sequence information of one or more subject(s) of the same species for which one or more modification(s) is known and e.g. associated with a malignant condition and/or a disease. For example, the database can contain nucleic acid sequence information of a healthy subject, e.g. a human or animal, and nucleic acid sequence information of a subject with a malignant condition and/or a disease, e.g. cancer and/or a heart disease. It is also not excluded that the database contains nucleic acid sequence information of the same subject from which the sample in the present method is obtained or provided, e.g. an older sample taken from the subject. The first reference database can contain the whole nucleic acid sequence information in regard to a subject or only a part thereof, e.g. the genome. Suitable databases include e.g. The Cancer Genome Atlas (TCGA; cancergenome.nih_gov/). Ensemble (www.ensembl_org), OMIM-Online Mendelian Inheritance in Man (www.omim_org/), METHHC, COSMIC (Catalogue of Somatic Mutations in Cancer), Cancer Gene Census (ongoing effort to catalogue those genes for which mutations have been causally implicated in cancer), dbSNP (Database of short genetic variations), ESP (Exome Sequencing Project), 1000 Genomes/10000 genomes (Deep catalogues of genetic variation), dbNSFP (annotation database for non-synonymous SNPs). Cancer Moonshot.

Also the second reference database is not particularly limited as long as it contains epigenetic information that allows correlation of the nucleic acid to a specific cell type, e.g. a cell of the lung, heart, kidney, liver, intestine, specific muscles, prostate, pancreas, testicles, larynx, pharynx, etc., i.e. any tissue. For example, according to certain embodiments even a link to cells of the blood can be made, e.g. red or white blood cells, so that also malignant conditions thereof can be detected, e.g. leukemia.

In this regard it is noted that epigenetic information can be easily linked to specific cell types, as e.g. disclosed in Lokk et al., "DNA methylome profiling of human tissues identifies global and tissue-specific methylation patterns". Genome Biology 15:3248, 2014, dx.doi_org//10.1186/gb-2014-15-4-r54, R. Lehmann-Werman et al., "Identification of tissue-specific cell death using methylation patterns of circulating DNA", PNAS, 113, 13. E1826-E1834, doi:10.1073/pnas.1519286113, or in Snyder et al., "Cell-free DNA Comprises an In Vivo Nucleosome Footprint that Informs Its Tissues-Of-Origin", Cell 164, 1-2, 57-68, 2016, dx.doi_org/ 10.1016/j.cell.2015.11.050. A suitable second reference database can be e.g. a methylation database like, for example, Methy Cancer, MethHC, MENT, MethylomeDB, NGSmethDB, DiseaseMeth, MethBase, TCGA. Like the first reference database the second reference database can contain information from healthy subjects and/or subjects negatively affected by a disease and/or malignant change. Also, again, older data of the same subject from which the sample in the present method is obtained or provided can be contained in the second reference database. It is not excluded in the present invention that a reference data base can contain data that make it suitable as first reference database as well as second reference database.

According to certain embodiments, the method of the first aspect allows determining a malfunction of a specific cell-type in a sample of a subject, e.g. a malignant condition like a tumor.

According to certain embodiments, a multitude of nucleic acids is obtained or provided in the present methods. This way the prediction of a disease and/or malignant condition in a specific cell type can be enhanced.

The linking of the one or more modification(s) of the at least one nucleic acid sequence to the specific cell type can be done in any way and can e.g. be simply carried out by combining the results of the comparison to the first and the second reference database. Also a link can be done to any further results of comparisons to further databases. In this way a direct correlation can be made between the tissue of origin of the at least one nucleic acid and a modification of the nucleic acid sequence thereof. In this way it is possible to find out if a medical condition arising from the modification of the nucleic acid sequence actually is problematic with regard to the tissue of origin or not. For example, modifications of the nucleic acid sequence of a cell free nucleic acid coming from lung cells can be indicative of lung cancer, whereas the same changes in cells from calve muscles could be without any adverse effect on the health of the subject. Thus, the present method allows not only determination of the possibility of adverse effects on the subject due to modifications of the nucleic acid sequence in a sample derived from a body fluid, but also the correlation to a specific tissue to determine whether the effect actually is adverse in the specific tissue. This way the results of the present methods can be used to form a basis for deciding whether a biopsy in a specific tissue could be useful even when no other symptoms with regard to the tissue are observed.

According to certain embodiments, the comparing the nucleic acid sequence to a first reference database of the subject to analyze it for a modification and the comparing the epigenetic profile of the at least one nucleic acid to a second database to correlate the at least one nucleic acid to a specific cell type are carried out simultaneously. This way it is possible to directly obtain results for deciding whether an acute action should be taken with regard to a medical condition, e.g. one affecting the heart or brain, etc.

According to certain embodiments, the linking of the one or more modification(s) of the at least one nucleic acid sequence of the specific cell-type of the subject is used to determine a malfunction of the specific cell-type of the subject, particularly a malignant condition. As already laid out above, it is possible to find out about malignant conditions with regard to a specific tissue, e.g. the liver, bladder, intestines, etc., for which a usual confirmation can be attributed with stress for the subject, e.g. due to invasive procedures.

According to certain embodiments, the subject in the present methods is a vertebrate, preferably a human or animal subject, particularly a human.

According to certain embodiments, the at least part of the epigenetic profile of said at least one nucleic acid is further compared to a third reference database to determine a malignant epigenetic change or another health-adverse change in the subject. As described above, it is known already that also specific epigenetic alterations are associated with malignant conditions, e.g. tumor. For example, a mutant allele-frequency can be 0.1% to 10% for cancer and other diseases or even below 0.1%, as disclosed by A. M. Newman et al., "Integrated digital error suppression for improved detection of circulating tumor DNA", Nature Biotechnology 34, 547-555, 2016, doi:10_1038/nbt_3520.

In this regard the third reference database is also not particularly limited and can be different from the first and/or second reference database or the same. It can also be integrated in the first and/or second reference database. Suitable examples are also e.g. mentioned with regard to the first and/or second reference database. Suitable databases include e.g. The Cancer Genome Atlas (TCGA; cancergenome.nih_gov/), or NIH Roadmap Epigenomics Mapping Consortium (egg2.wustl_edu/roadmap/web_portal/), etc., as e.g. described above.

According to certain embodiments, the at least part of the epigenetic profile is a methylation pattern of the DNA sequence. Particularly the methylation pattern allows an easy link to the cell type.

In a second aspect the present invention relates to a method of determining a malignant condition of a specific cell type in a subject, comprising:

obtaining or providing a sample from the subject comprising at least one nucleic acid;

sequencing the at least one nucleic acid from the sample to obtain the nucleic acid sequence of said at least one nucleic acid, and determining at least a part of the epigenetic profile of said at least one nucleic acid;

comparing said nucleic acid sequence to a first reference database to determine one or more modification(s) thereof that are indicative of a malignant condition;

comparing the at least part of the epigenetic profile of said at least one nucleic acid to a second reference database to correlate said at least one nucleic acid to a specific cell type; and linking the one or more modification(s) of the at least one nucleic acid sequence that are indicative of a malignant condition to the specific cell type.

With regard to the method of the second aspect, the different steps identical to the ones in the first method can be carried out in the same way, i.e. the obtaining or providing a sample from the subject comprising at least one nucleic acid; the sequencing the at least one nucleic acid from the sample to obtain the nucleic acid sequence of said at least one nucleic acid, and determining at least a part of the epigenetic profile of said at least one nucleic acid; the comparing said nucleic acid sequence to a first reference database to determine one or more modification(s) thereof that are indicative of a malignant condition; and the comparing the at least part of the epigenetic profile of said at least one nucleic acid to a second reference database to correlate said at least one nucleic acid to a specific cell type. Thus, all embodiments mentioned with regard to the method of the first method also apply to the method of the second aspect.

The linking of the one or more modification(s) of the at least one nucleic acid sequence that are indicative of a malignant condition to the specific cell type can be carried out in any suitable way and is not particularly limited. It can be e.g. just a combination of the data obtained when comparing the nucleic acid sequence to the first reference database (first data) and the data obtained when comparing the at least part of the epigenetic profile of said at least one nucleic acid to the second reference database (second data), wherein the first data can e.g. indicate a possible malignant condition and the second data can indicate the cell type. With the method of the second aspect the malignant condition is directly linked to a specific cell type. This in return means that—in contrast to the method of the first aspect—a modification of the nucleic acid sequence that possibly can indicate a malignant change in one cell type but not the specific cell type determined when comparing the at least part of the epigenetic profile of said at least one nucleic acid to the second reference database is not determined in the method of the second aspect. This can be done e.g. by filtering the corresponding result in the step of linking the one or more modification(s) of the at least one nucleic acid sequence that are indicative of a malignant condition to the specific cell type, i.e. results indicative of a possible malignant condition, e.g. having a specific modification pattern, that are known to not lead to a malignant condition in the specific cell type determined.

According to certain embodiments, the comparing the nucleic acid sequence to a first reference database of the subject to analyze it for a modification and the comparing the epigenetic profile of the at least one nucleic acid to a second database to correlate the at least one nucleic acid to a specific cell type are carried out simultaneously, as described correspondingly in the method of the first aspect.

According to certain embodiments, the subject in the method of the second aspect is a vertebrate, preferably a human or animal subject, particularly a human.

As in the method of the first aspect, the at least part of the epigenetic profile of said at least one nucleic acid can be further compared to a third reference database to determine a malignant epigenetic change in the method of the second aspect. The third reference database can be, as well as the first and second reference databases, the same as described with regard to the method of the first aspect.

In a third aspect a method of linking one of more modification(s) of at least one nucleic acid sequence in a sample of a subject to a specific cell type of the subject is disclosed, comprising:

obtaining or providing at least one nucleic acid se-quence of a nucleic acid and at least a part of the epigenetic profile of said at least one nucleic acid;

comparing said nucleic acid sequence to a first reference database to determine one or more modification(s) thereof;

comparing the at least part of the epigenetic profile of said at least one nucleic acid to a second reference database to correlate said at least one nucleic acid to a specific cell type; and linking the one or more modification(s) of the at least one nucleic acid sequence to the specific cell type.

In this regard the obtaining or providing at least one nucleic acid sequence of a nucleic acid and at least a part of the epigenetic profile of said at least one nucleic acid are not particularly limited. For example, the nucleic acid sequence and the at least part of the epigenetic profile can be obtained or provided as data output from a sequencing method, e.g. one as described with regard to the method of the first aspect. The data can be in any form as long as they can be used for the subsequent comparison steps, e.g. are machine-readable.

The comparing said nucleic acid sequence to a first reference database to determine one or more modification(s) thereof, the comparing the at least part of the epigenetic profile of said at least one nucleic acid to a second reference database to correlate said at least one nucleic acid to a specific cell type, and the linking the one or more modifi-cation(s) of the at least one nucleic acid sequence to the specific cell type can be carried out in the same way as described with regard to the first aspect of the invention.

According to certain embodiments, the comparing the nucleic acid sequence to a first reference database of the subject to analyze it for a modification and the comparing the epigenetic profile of the at least one nucleic acid to a second database to correlate the at least one nucleic acid to a specific cell type are carried out simultaneously, as described with regard to the first aspect. Furthermore, the at least part of the epigenetic profile of said at least one nucleic acid can be further compared to a third reference database to determine a malignant epigenetic change, also as described with regard to the first, respectively second, aspect.

In a further aspect the present invention relates to a computer program product comprising computer executable instructions which, when executed, perform a method according to the third aspect.

According to certain embodiments the computer program product is one on which program commands or program codes of a computer program for executing said method are stored. According to certain embodiments the computer program product is a storage medium. The computer pro-gram product of the present invention can be self-learning, e.g. incorporating data obtained in the method of the third aspect in the first, second and/or third reference database.

A workflow as described with regard to the aspects of the present invention can be included and/or integrated in pre-vention examinations for cancer and other diseases, particu-larly when becoming more cost-effective. The tissue-spe-cific alteration allows even to detect tissue-specific malignant DNA and methylation changes even when there is no detectable phenotype. This means that a cancer/disease can be detected in an early stage even when e.g. diagnostic imaging does not result in a positive result if the primary tumor is very small.

FIG. 1 shows schematically a workflow for an enhanced liquid biopsy 100 with regard to the methods of the present invention, with methylation as an example for an epigenetic alteration.

As shown in FIG. 1, nucleic acids 1, e.g. circulating DNA and/or RNA molecules, are sequenced using a sequencing 2 method that also allows determination of the methylation status of the nucleic acids, e.g. using a DNA/RNA base and methylation caller. This way, nucleic acid (e.g. DNA and/or RNA) sequence reads 3 including methylation data are obtained, wherein the methylation M is indicated by a star in the figure. The obtained data are then compared in a comparison step 6 to a second reference database 4, e.g. a tissue-specific methylation database, and a first reference database 5, e.g. a disease-specific nucleic acid change database, using a suitable comparison means, e.g. a computer program product, e.g. a sequence classifier. In this case the first reference database can also contain disease-specific methylation changes, i.e. also function as a third reference database. As a result of the comparison the nucleic acids 1, respectively the data obtained therefrom, can afterwards be divided with regard to the results obtained in inconspicuous nucleic acids 7, and nucleic acids 8 containing modifications that can be indicative of a cancer 9, e.g. of the lung 9a, the intestine 9b or the liver 9c—as indicated by the difference in methylation pattern, or a disease 10, e.g. dilated cardiomyopathy, indicated by different methylation patterns 10a, 10b and 10c with regard to nucleic acids originating from the heart.

Figure 2:
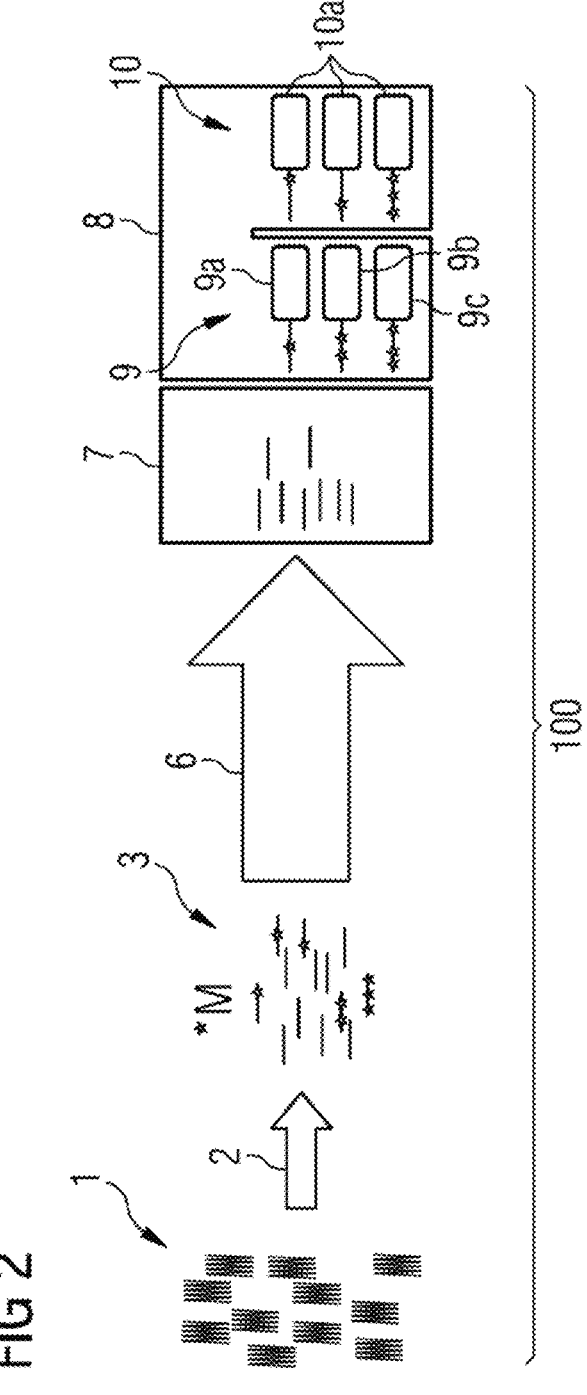
FIG. 2 shows schematically details of FIG. 1.

FIG. 2 shows a detail of FIG. 1 wherein the databases are omitted for clarity, only showing the actual steps of sequencing 2 and comparison 6 and the respective results obtained from the nucleic acids 1, as indicated already in FIG. 1, showing how the nucleic acids 1 are first "translated" in nucleic acid sequence reads 3 and then classified in inconspicuous nucleic acids 7 and nucleic acids containing modifications 8.

Figure 3:
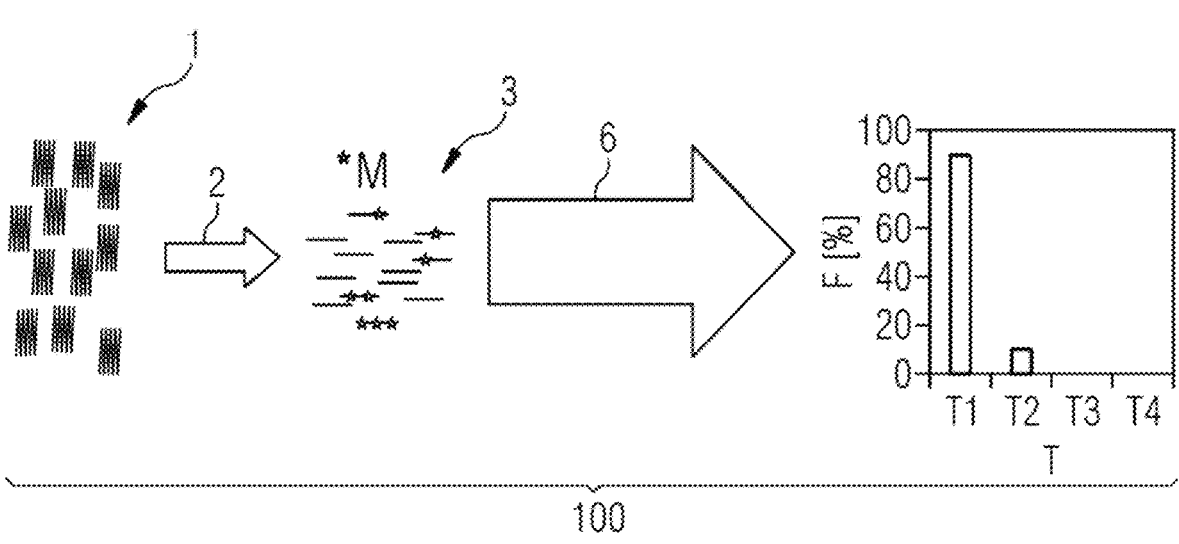
FIG. 3 gives reference to the features of FIG. 2 with regard to actual results that can be obtained by the present method.

FIG. 3 gives reference to the features of FIG. 2 with regard to actual results that can be obtained by the present method. As can be seen in the figure, data are obtained in the comparison 6 that can then be statistically analyzed using a suitable method to e.g. determine the fraction F of a specific tissue T in the nucleic acids 1 contained in a sample, indicating that the amount of specific nucleic acids is increased. For example, in the figure, T1 can refer to leukocytes, T2 can refer to the lung, T3 to the kidneys and T4 to the prostate, indicating an increased amount of free nucleic acids originating from the lung in the body fluid sample as compared to the kidneys and prostate. Taken together with the data for modification of the nucleic acid sequence, this can then e.g. indicate lung cancer if the nucleic acids originating from the lung also contain modifications indicative of cancer.

Figure 4:
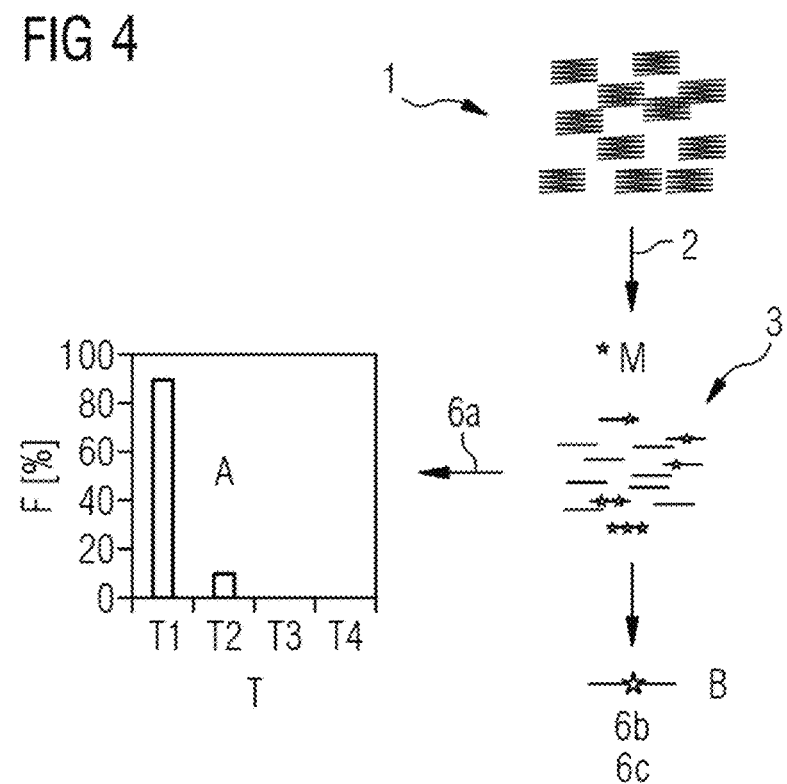
FIG. 4 gives a detail schematic view of the processes in FIG. 3.

FIG. 4 gives a detail schematic view of the processes in FIG. 3. It shows thereby that not only statistical data A, as indicated in FIG. 3, are obtained for all nucleic acids in the comparison step 6, e.g. when identifying the tissue of origin, step 6a, but also that for each single nucleic acid/fragment/ read B the methylation information 6B, i.e. indicating the lung and possibly a malignant change thereof, as well as the nucleic acid sequence information 6C, e.g. indicating a TP53 mutation, is obtained.

The above embodiments can be combined arbitrarily, if appropriate. Further possible embodiments and implementations of the invention comprise also combinations of features not explicitly mentioned in the foregoing or in the following with regard to the Examples of the invention. Particularly, a person skilled in the art will also add individual aspects as improvements or additions to the respective basic form of the invention.

Illustrative Embodiments

Provided here are illustrative embodiments of the disclosed technology. These embodiments are illustrative only and do not limit the scope of the present disclosure or of the embodiments attached hereto.

Embodiment 1. A method of determining one or more modification(s) of the nucleic acid sequence of at least one nucleic acid and at least one epigenetic alteration of said at least one nucleic acid in a sample of a subject, wherein the sample is derived from a body fluid of the subject, comprising: a) obtaining or providing a sample from the subject comprising at least one nucleic acid; b) sequencing the at least one nucleic acid from the sample to obtain the nucleic acid sequence of said at least one nucleic acid, and determining at least a part of the epigenetic profile of said at least one nucleic acid; c) comparing said nucleic acid sequence to a first reference database to determine one or more modification(s) thereof; d) comparing the at least part of the epigenetic profile of said at least one nucleic acid to a second reference database to correlate said at least one nucleic acid to a specific cell type; and e) linking the one or more modification(s) of the at least one nucleic acid sequence to the specific cell type.

Embodiment 2. The method of embodiment 1, wherein the comparing of the nucleic acid sequence to a first reference database of the subject to analyze it for a modification and the comparing of the epigenetic profile of the at least one nucleic acid to a second database to correlate the at least one nucleic acid to a specific cell type are carried out simultaneously.

Embodiment 3. The method of embodiments 1 or 2, wherein the linking of the one or more modification(s) of the at least one nucleic acid sequence of the specific cell-type of the subject is used to determine a malfunction of the specific cell-type of the subject, particularly a malignant condition.

Embodiment 4. The method of any one of embodiments 1 to 3, wherein the subject is a vertebrate, preferably a human or animal subject, particularly a human.

Embodiment 5. The method of any one of embodiments 1 to 4, wherein the at least part of the epigenetic profile of said at least one nucleic acid is further compared to a third reference database to determine a malignant epigenetic change.

Embodiment 6. The method of any one of embodiments 1 to 5, wherein the at least part of the epigenetic profile is a methylation pattern of the DNA sequence.

Embodiment 7. The method of any one of embodiments 1 to 6, wherein the sequencing the at least one nucleic acid from the sample to obtain the nucleic acid sequence of said at least one nucleic acid, and determining at least a part of the epigenetic profile of said at least one nucleic acid is carried out using a method selected from nanopore sequencing, single-molecule based sequencing, tunneling based detection or combinations thereof.

Embodiment 8. A method of determining a malignant condition of a specific cell type in a subject, comprising: a) obtaining or providing a sample from the subject comprising at least one nucleic acid; b) sequencing the at least one nucleic acid from the sample to obtain the nucleic acid sequence of said at least one nucleic acid, and determining at least a part of the epigenetic profile of said at least one nucleic acid; c) comparing said nucleic acid sequence to a first reference database to determine one or more modification(s) thereof that are indicative of a malignant condition; d) comparing the at least part of the epigenetic profile of said at least one nucleic acid to a second reference database to correlate said at least one nucleic acid to a specific cell type; and e) linking the one or more modification(s) of the at least one nucleic acid sequence that are indicative of a malignant condition to the specific cell type.

Embodiment 9. The method of embodiment 8, wherein the comparing of the nucleic acid sequence to a first reference database of the subject to analyze it for a modification and the comparing of the epigenetic profile of the at least one nucleic acid to a second database to correlate the at least one nucleic acid to a specific cell type are carried out simultaneously.

Embodiment 10. The method of embodiment 8 or 9, wherein the subject is a vertebrate, preferably a human or animal subject, particularly a human.

Embodiment 11. The method of any one of embodiments 8 to 10, wherein the at least part of the epigenetic profile of said at least one nucleic acid is further compared to a third reference database to determine a malignant epigenetic change.

Embodiment 12. A method of linking one of more modification(s) of at least one nucleic acid sequence in a sample of a subject to a specific cell type of the subject, comprising: a) obtaining or providing at least one nucleic acid sequence of a nucleic acid and at least a part of the epigenetic profile of said at least one nucleic acid; b) comparing said nucleic acid sequence to a first reference database to determine one or more modification(s) thereof; c) comparing the at least part of the epigenetic profile of said at least one nucleic acid to a second reference database to correlate said at least one nucleic acid to a specific cell type; and d) linking the one or more modification(s) of the at least one nucleic acid sequence to the specific cell type.

Embodiment 13. The method of embodiment 12, wherein the comparing of the nucleic acid sequence to a first reference database of the subject to analyze it for a modification and the comparing of the epigenetic profile of the at least one nucleic acid to a second database to correlate the at least one nucleic acid to a specific cell type are carried out simultaneously.

Embodiment 14. The method of embodiment 12 or 13, wherein the at least part of the epigenetic profile of said at least one nucleic acid is further compared to a third reference database to deter mine a malignant epigenetic change. Embodiment 15. Computer program product comprising computer executable instructions which, when executed, perform a method according to any one of embodiments 12 to 14.

EXAMPLES

The present invention will now be described in detail with reference to several examples thereof. However, these examples are illustrative and do not limit the scope of the invention.

A blood sample from a human patient is provided for lung cancer screening. The screening test aims to determine alterations associated with the nucleic acids, methylation profile, and to conclude the tissue of origin of the nucleic acids to strengthen cancer screening by multiple evidence levels.

After separation of the nucleic acids, two methods are em-ployed for the scalpel-free biopsy, 1) bisulfite sequencing (comparative example) and 2) direct nanopore sequencing (example).

1) For bisulfite-sequencing, an estimate of sequencing depths is more cumbersome when the aim of the experiment is to analyze all three levels, nucleic acid (e.g. DNA) sequence mutation, epigenetic profile change and tissue of origin, since a new variable has to be considered: the reaction efficiency of bisulfite conversion. Incomplete deamination might occur at low mutant allele frequency and low cfDNA pools, as described also in e.g. R. P. Darst et al., "Bisulfite Sequencing of DNA, Curr. Protoc. Mol. Biol, doi: 10_1002/0471142727_mb0709s91. Second, the conversion of non-methylated C masks real cancer-derived C->T mutations that might be indicative for cancer. Hence, for an accurate determination of mutation within a liquid biopsy the experiment might need to be done twice, with and without bisulfite conversions, thus also doubling the price. Also, the joint analysis of both data sets is not based on the same DNA fragments, making it more challenging to analyze both.

2) The extracted nucleic acids are sequenced without prior bisulfite conversion with nanopore sequencing with indirect detection using ion current alteration, (e.g. using Oxford Nanopore MinION. This method allows detecting epigenetic modifications (e.g. methylated C) and a non-modified DNA sequence simultaneously. Hence, there is little bias introduced due to a conversion, and hence C->T mutations are better to call. In contrast to the bisulfite sequencing, the method was less tedious and required less material.

Both methods detected an EGFR mutation indicative for lung cancer: EGFR c.2573T>G (L858R). Also, an increased level of methylation of the DCC promoter was detected that gave an additional level of confidence of the presence lung cancer. A third level of confidence was gathered when specific methylation profile of the TSLP was identified, which differently methylated human blood and human lung tissue.

With the present invention it is possible to integrate two till now independently measured entities, i.e. nucleic acid, e.g. DNA, sequence and epigenetic patterns. The analysis of these features originate thereby from the same molecule/fragment/read, so that a direct link is possible between modifications of the nucleic acid sequence and the cell type. Linking nucleic acid, e.g. cfDNA, molecules and detected somatic mutations to the tissue of origin thereby facilitates a "liquid tissue biopsy". Using a method that detects both, the nucleic acid sequence and an epigenetic pattern, leads to a more efficient, cost effective method with less bias and less chance of artefacts.

The invention claimed is:

1. A method of linking one or more modification(s) of the nucleic acid sequence of at least one nucleic acid and at least one epigenetic alteration of said at least one nucleic acid in a sample of a subject to a specific cell type, comprising:
   a) sequencing at least one nucleic acid from a sample derived from a body fluid of the subject to obtain the nucleic acid sequence of said at least one nucleic acid and to obtain at least a part of an epigenetic profile of said at least one nucleic acid;

b) comparing said nucleic acid sequence to a first reference database to obtain one or more modification(s) thereof, wherein the first reference database is selected from the group of databases consisting of The Cancer Genome Atlas; Ensemble; Online Mendelian Inheritance in Man (OMIM); MethHC; Catalogue of Somatic Mutations in Cancer (COSMIC); Cancer Gene Census; Database of short genetic variations (dbSNP); Exome Sequencing Project (ESP); 1000 Genomes; 10000 genomes; database for non-synonymous SNPs (dbNSFP); and Cancer Moonshot;

c) comparing the at least part of the epigenetic profile of said at least one nucleic acid to a second reference database comprising a methylation database to obtain a specific cell type associated with the at least part of the epigenetic profile; and d) linking the one or more modification(s) of the at least one nucleic acid sequence obtained in step b) to the specific cell type of step c);

wherein the sequencing of the at least one nucleic acid from the sample to obtain the nucleic acid sequence of said at least one nucleic acid and to obtain the at least part of an epigenetic profile of said at least one nucleic acid corresponding to a specific cell type is carried out using a method selected from nanopore sequencing, single-molecule based sequencing, tunneling based detection or any combination thereof, and wherein step b) and step c) are carried out simultaneously.

2. The method of claim 1, wherein the linking of the one or more modification(s) of the at least one nucleic acid sequence of the specific cell type of the subject is used to determine a malfunction of the specific cell type of the subject.

3. The method of claim 1, wherein the subject is a human.

4. The method of claim 1, wherein the at least part of the epigenetic profile of said at least one nucleic acid is further compared to a third reference database to determine a malignant epigenetic change.

5. The method of claim 1, wherein the at least part of the epigenetic profile is a methylation pattern of the nucleic acid sequence.

6. The method of claim 1, wherein the nucleic acid sequence of said at least one nucleic acid and the at least a part of the epigenetic profile of said at least one nucleic acid corresponding to a specific cell type are simultaneously obtained.

7. The method of claim 1, wherein the one or more modification(s) of the at least one nucleic acid sequence obtained in step b) comprises single nucleotide deletion, insertion, or substitution.

8. A method of determining a malignant condition of a specific cell type in a subject, comprising:

a) sequencing at least one nucleic acid from a sample derived from a body fluid of the subject to obtain the nucleic acid sequence of said at least one nucleic acid and to obtain at least a part of an epigenetic profile of said at least one nucleic acid;

b) comparing said nucleic acid sequence to a first reference database to obtain one or more modification(s) thereof that are indicative of a malignant condition, wherein the first reference database is selected from the group of databases consisting of The Cancer Genome Atlas; Ensemble; Online Mendelian Inheritance in Man (OMIM); MethHC; Catalogue of Somatic Mutations in Cancer (COSMIC); Cancer Gene Census; Database of short genetic variations (dbSNP); Exome Sequencing Project (ESP); 1000 Genomes; 10000 genomes; database for non-synonymous SNPs (dbNSFP); and Cancer Moonshot;

c) comparing the at least part of the epigenetic profile of said at least one nucleic acid to a second reference database comprising a methylation database to obtain a specific cell type associated with the at least part of the epigenetic profile; and d) linking the one or more modification(s) of the at least one nucleic acid sequence that are indicative of a malignant condition obtained in step b) to the specific cell type obtained in step c);

wherein the sequencing of the at least one nucleic acid from the sample to obtain the nucleic acid sequence of said at least one nucleic acid and to obtain the at least part of an epigenetic profile of said at least one nucleic acid corresponding to a specific cell type is carried out using a method selected from nanopore sequencing, single-molecule based sequencing, tunneling based detection or combinations thereof, and wherein step b) and step c) are carried out simultaneously.

9. The method of claim 8, wherein the subject is a human.

10. The method of claim 8, wherein the at least part of the epigenetic profile of said at least one nucleic acid is further compared to a third reference database to determine a malignant epigenetic change.

11. The method of claim 8, wherein the nucleic acid sequence of said at least one nucleic acid and the at least a part of the epigenetic profile of said at least one nucleic acid corresponding to a specific cell type are simultaneously obtained.

12. The method of claim 8, wherein the one or more modification(s) of the at least one nucleic acid sequence obtained in step b) comprises single nucleotide deletion, insertion, or substitution.

13. A method for locating malignant disease in a subject, the method comprising:

a) obtaining (i) a sequence and (ii) at least a part of an epigenetic profile of at least one nucleic acid from a sample from the subject using nanopore sequencing, single-molecule based sequencing, tunneling based detection or combinations thereof;

b) detecting one or more sequence modification(s) in the at least one nucleic acid using a first reference database, wherein the first reference database is selected from the group of databases consisting of The Cancer Genome Atlas; Ensemble; Online Mendelian Inheritance in Man (OMIM); MethHC; Catalogue of Somatic Mutations in Cancer (COSMIC); Cancer Gene Census; Database of short genetic variations (dbSNP); Exome Sequencing Project (ESP); 1000 Genomes; 10000 genomes; database for non-synonymous SNPs (dbNSFP); and Cancer Moonshot;

c) detecting a specific cell type for the at least one nucleic acid using a second reference database, wherein the second reference database comprises a methylation database; and d) locating the malignant disease by linking the one or more sequence modification(s) detected in b) to the specific cell type detected in c), wherein step b) and step c) are carried out simultaneously.

14. The method of claim 13, wherein obtaining (i) the sequence and (ii) at least a part of the epigenetic profile of the at least one nucleic acid occur simultaneously.

15. The method of claim 13, wherein the one or more sequence modification(s) comprises single nucleotide deletion, insertion, or substitution.

16. The method of claim 13, wherein the methylation database is selected from the group consisting of Methy-Cancer; MethHC; Methylation and Expression database of Normal and Tumor tissues (MENT), MethylomeDB, NGS-methDB, DiseaseMeth, MethBase, The Cancer Genome Atlas (TCGA), and NIH Roadmap Epigenomics Mapping Consortium.

17. The method of claim 13, further comprising detecting malignant epigenetic change from a third reference database using the at least a part of the epigenetic profile of the at least one nucleic acid.

18. The method of claim 13, wherein the at least part of the epigenetic profile is a methylation pattern of the nucleic acid sequence.

19. The method of claim 13, wherein the subject is a human.

\*    \*    \*    \*    \*